(12) United States Patent
Apel et al.

(10) Patent No.: US 8,329,296 B2
(45) Date of Patent: Dec. 11, 2012

(54) PRIMARY PARTICLES COATED WITH A CHROMOPHORIC COMPONENT

(75) Inventors: Elke Apel, Sevelen (CH); Christian Ritzberger, Nenzing (AT); Wolfram Holand, Schaan (LI); Christoph Appert, Vaduz (LI); Wolfgang Wachter, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 12/397,861

(22) Filed: Mar. 4, 2009

(65) Prior Publication Data
US 2010/0025874 A1 Feb. 4, 2010

(30) Foreign Application Priority Data
Jul. 30, 2008 (EP) .................................. 08161501

(51) Int. Cl.
*B32B 5/16* (2006.01)
*C04B 35/488* (2006.01)
(52) U.S. Cl. ......................... 428/403; 428/702; 501/103
(58) Field of Classification Search .................. 428/403, 428/702; 501/103
See application file for complete search history.

(56) References Cited

U.S. PATENT DOCUMENTS

| 4,851,293 | A | * | 7/1989 | Egerton et al. ................ 428/403 |
| 5,011,403 | A | * | 4/1991 | Sadoun et al. ..................... 433/8 |
| 5,137,575 | A | | 8/1992 | Yasuki |
| 5,206,192 | A | * | 4/1993 | Dransfield et al. ............ 501/103 |
| 5,320,675 | A | * | 6/1994 | Dransfield et al. ............ 106/450 |
| 5,496,682 | A | | 3/1996 | Quadir |
| 5,744,233 | A | * | 4/1998 | Opitz et al. .................... 428/328 |
| 6,709,694 | B1 | * | 3/2004 | Suttor et al. ................. 427/2.26 |
| 6,713,421 | B1 | | 3/2004 | Hauptmann et al. |
| 7,497,983 | B2 | * | 3/2009 | Khan et al. ..................... 264/673 |
| 8,173,562 | B2 | * | 5/2012 | Holand et al. ................. 501/103 |
| 2006/0117989 | A1 | | 6/2006 | Hauptmann et al. |
| 2007/0087196 | A1 | * | 4/2007 | Ruehle et al. ................. 428/403 |
| 2007/0272120 | A1 | | 11/2007 | Engels et al. |
| 2007/0292597 | A1 | | 12/2007 | Ritzberger et al. |
| 2008/0032047 | A1 | * | 2/2008 | Parashar et al. ............ 427/372.2 |
| 2008/0138768 | A1 | | 6/2008 | Holand et al. |
| 2010/0040767 | A1 | | 2/2010 | Uibel |

FOREIGN PATENT DOCUMENTS

| DE | 199 50 284 A1 | 4/2001 |
| EP | 0 535 796 A2 | 4/1993 |
| GB | 421 872 | 1/1935 |
| JP | 01009839 | 1/1989 |
| WO | 2007/112885 A1 | 10/2007 |
| WO | 2008/023053 A2 | 2/2008 |

OTHER PUBLICATIONS

Beil, Fortschritt-Berichte VDI (2002).
Fouassier, eds., Radiation Curing in Polymer Science and Technology, vol. II, London and New York, NY:Elsevier Applied Science (1993).
Gebhardt, "Vision Rapid Prototyping," DKG 83(13):7-12 (2006).
Gebhardt, Generative Fertigungsverfahren, 3rd Ed., Munchen, Germany:Hanser (2007).
Moreno "The Role of Slip Additives in Tape Casting Technology: Part II—Binders and Plasticizers," Amer. Ceram. Soc. 72(11):1647-1657 (1992).

* cited by examiner

*Primary Examiner* — Hoa (Holly) Le
(74) *Attorney, Agent, or Firm* — Ann M. Knab; Thad McMurray

(57) ABSTRACT

The invention relates to primary particles of oxide-ceramic material, wherein the primary particles have an average particle size in the range from 10 to 1000 nm and are coated with a chromophoric component, a process for their preparation and their use in particular in the preparation of ceramic moldings and dental restorations. The invention further relates to a suspension based on oxide-ceramic material which contains the primary particles, and a process for the preparation of a ceramic moldings.

7 Claims, No Drawings

PRIMARY PARTICLES COATED WITH A CHROMOPHORIC COMPONENT

This application claims the benefit of European Patent Application Serial No. 08161501.5, filed Jul. 30, 2008, which is hereby incorporated by reference in its entirety.

FIELD

The invention relates to primary particles which are coated with a chromophoric component, a process for their preparation and their use, in particular in the preparation of ceramic mouldings and dental restorations. The invention further relates to a suspension, based on oxide-ceramic material, which contains the primary particles, and a process for the preparation of a ceramic mouldings.

BACKGROUND

In restorative dentistry, high-performance ceramics such as $Al_2O_3$ and tetragonal $ZrO_2$ have become very important for the manufacture of wide-span bridges and high-load-bearing crowns. The emphasis will be on the processing of $ZrO_2$ materials below. These dental restorations are preferably prepared by machine-processing of $ZrO_2$ blanks which are produced from granulated $ZrO_2$ powders by pressing followed in most cases by thermal treatment.

Various methods for colouring oxide-ceramic powder such that the moulding prepared therefrom has the desired colour are known from the state of the art.

The best-known method is the admixing of colouring oxides into the granular material of the oxide ceramic. After it is pressed, processed and thermally treated, the finished coloured moulding then forms. As a result of the thermal treatment, the colouring ions cover a lattice site or an interstitial site. The most important documents for this are: U.S. Pat. Nos. 5,219,805 or 5,263,858, 5,656,564 or 5,059,562 or 5,118,457.

Further approaches have been proposed for the preparation of coloured ceramic mouldings, in particular dental mouldings, the colouring of which comes as close as possible to that of natural teeth. Thus processes are known from the state of the art according to which coloured blanks or also dental restoration parts are obtained by infiltrating liquids into a presintered moulding (U.S. Pat. No. 6,709,694 and EP 1 486 476 respectively). However, these processes have the disadvantage that colouring takes place after the presintering process and thus liquids are introduced into an open-pored ceramic body. Thus the colouring is not completely homogeneous. Nor can polychromatism be achieved. In particular, by subsequently colouring a partly blank or a shaped dental product, it can be that only the cavities (pores) between the partially co-sintered particles of the starting powder are covered by the colouring materials. Thus also only discrete areas of the surface of the particles are coloured with a layer of the colouring oxides, but a continuous covering of the surface of the particles of the starting powder is not possible. A further great disadvantage with an infiltration is the concentration gradient of the colouring from the outside in. If a porous body is introduced into the colouring solution, the starting solution releases some of the dissolved colouring ions on entering the body and is thus "depleted" of colouring substances from the outside in. Consequently there is a higher concentration of the colouring ions and oxides outside than inside the moulding. Furthermore only a certain penetration depth can be achieved by means of the infiltration technique.

EP 1 859 757 A2 describes a process for the preparation of coloured blanks and dental mouldings. Oxide-ceramic powders in granular form are coated with a chromophoric substance in aqueous solution in a fluid-bed reactor. The thus-obtained coated granular material is then pressed to form a moulding which can be further processed to form a dental spacer after a presintering by milling or grinding.

The mouldings prepared by compression processes are usually obtained in the form of block bodies from which the desired restorations can be milled, for example using CAD/CAM. Such block bodies, even with a continuous colouring, are described for example in EP 1 859 758 A1. The disadvantage of this technique is in particular the considerable loss of valuable sinter ceramic associated with the milling process.

In addition to the dry-pressing processes, the use of ceramic particles in suspensions, in particular in the form of so-called slips, is also known in the state of the art. It can be advantageous here to apply to the ceramic particles a coating which can serve for example as a processing aid. Thus DE 10 2005 003 755 A1 describes a process for coating a dental powder with inorganic substances such as Bronsted or Lewis acids or bases, or organic substances, in particular certain polymers. The coating takes place in each case using an aqueous solution of the coating component either directly by introduction of the powder into the aqueous medium or by a fluid-bed process.

Furthermore, a process is known from EP 1 210 054 according to which the coloured blanks are prepared from partially stabilized zirconium dioxide such that the starting materials are dissolved in water in the form of their soluble chlorides, including the colouring substances, a co-precipitation is carried out and the precipitation product is calcined at approx. 700° C. After the grinding of the calcinate and a spray-drying, the thus-obtained granular material is isostatically pressed and then thermally treated (debinding and presintering).

In dental engineering, the most common method to date is the grinding or milling of blocks, plates or cylinders. The decision as to which type of mechanical processing is chosen depends on the respective machines, but also on the state of the oxide ceramic (ratio of the density of the part to be processed to the theoretically achievable density).

The so-called constructive or generative manufacturing processes represent a further approach to the formation of oxide-ceramic mouldings. The term "Rapid Prototyping" (RP) covers generative manufacturing processes in which 3-dimensional models or components are prepared from computer-aided design data (CAD data) (A. Gebhardt, Vision of Rapid Prototyping, Ber. DGK 83 (2006) 7-12). These are processes such as e.g. stereolithography (SL), selective laser sintering (SLS), 3D printing, fused deposition modelling (FDM), ink-jet printing (IJP), 3-D plotting, multi-jet modelling (MJM), solid freeform fabrication (SFF), laminated object manufacturing (LOM), laser powder forming (LPF) and direct ceramic jet printing (DCJP), with which models, components or mouldings can be prepared cheaply even on a small scale (A. Gebhardt, Generative Fertigungsverfahren, $3^{rd}$ ed., Carl Hanser Verlag, Munich 2007, 77 et seq.). Stereolithography involves RP processes (A. Beil, Fertigung von Mikro-Bauteilen mittels Stereolithographie, Düsseldorf 2002, VDI-Verlag 3 et seq.) in which a mouldings is constructed in layers from a liquid and curable monomer resin on the basis of CAD data.

RP processes for the preparation of dental mouldings such as inlays, crowns or bridges are highly advantageous particularly with ceramic materials, because the impression-taking and casting processes and the grinding and milling operations respectively, which involve considerable manual outlay in the dental engineering laboratory, can thus be greatly simplified and at the same time the material loss which occurs with non-generative processes can be avoided. As a complete digital process chain is in place today, the standard process steps for the preparation of e.g. multi-unit bridge frameworks (alignment in the articulator, wax modulation, embedding and casting) can be replaced by the digitalization of the model, virtual design of the dental moulding and its generative stereolithographic manufacture.

Both stereolithography and increasingly also 3D printing have proved to be important methods for preparing dental mouldings from oxide-ceramic materials. Sprayable ceramic inks which contain oxide-ceramic particles in a cross-linkable solvent are used for 3D printing. After a layer has been deposited, curing takes place by high-energy radiation. In contrast, in stereolithography a layer of a cross-linkable slip is cured by targeted illumination.

The composition of the slips and of the ceramic inks are substantially the same, at least in respect of the components used. These are in both cases the oxide-ceramic particles, a cross-linkable monomer or monomer mixture, an initiator or initiator system and optionally further auxiliaries such as solvents etc.

In the preparation of ceramic mouldings e.g. by means of stereolithography, a ceramic green compact is firstly prepared by layered curing of a free-flowing ceramic slip which is then sintered after debinding to form a dense ceramic moulding. The green compact is also called a green body. The term debinding is used to describe the elimination of the binder. Here, the binder used is usually removed by heating the green compact to a temperature of approx. 90° C. to 600° C. It is essential that the formation of cracks and deformations is very largely avoided. The green compact becomes the so-called white body as a result of the debinding.

In debinding, purely thermal and thermochemical processes take place. Mixtures of water, solvents, polymers, waxes or oils are usually used as binders in the pressing of ceramic powders. Polypropylene, polyethylene, polyvinyl acetate, polyvinyl alcohol, methylcellulose, polyvinylpyrrolidone, polystyrene or polyethyl methacrylate are mostly used as polymers (cf. R. Moreno, Amer. Cer. Soc. Bull. 71 (1992) 1647-1657). These are linear polymers which are broken down more or less easily into volatile components by depolymerization or chain-splitting at increased temperature.

In the case of green bodies produced by RP processes based on cross-linking monomer mixtures, there is a polymer network. Through the use of cross-linking monomers the curing time which is required to obtain a stable solid can be significantly shortened, but at the same time the polymer network that forms also displays a much higher thermal stability compared with linear polymers, which adversely affects the debinding process.

The sintering of the white body takes place in the sintering furnace during high-temperature firing. The finely-distributed ceramic powder is compacted and solidified by exposure to temperature below the melting temperature of the main component, as a result of which the porous component becomes smaller and its strength increases.

U.S. Pat. No. 5,496,682 discloses light-curable compositions for the preparation of three-dimensional bodies by stereolithography, which contain 40 to 70 vol.-% ceramic or metal particles, 10 to 35 wt.-% monomer, 1 to 10 wt.-% photoinitiator, 1 to 10 wt.-% dispersant and preferably also solvent, plasticizer and coupling agent.

DE 10 2006 015 014 A1 describes a process for the preparation of three-dimensional ceramic mouldings by layered imprinting of a suspension with the help of an ink-jet printer. The suspension contains ceramic particles in a dispersant medium based on an aqueous boehmite sol.

U.S. Pat. No. 6,117,612 discloses resins for the stereolithographic preparation of sintered ceramic or metal parts. The resins have a viscosity of less than 3000 mPa·s. For their preparation, monomers with a low viscosity are used, preferably in aqueous solution. A high solids content and low viscosity are said to be achieved through the use of dispersants.

DE 199 50 284 A1 describes compositions curable with visible light based on polymerizable monomers or oligomers and their use for the preparation of dental restorations made of plastic materials with RP processes.

A particular problem in the preparation of ceramic spacers by RP processes is the colouring of the ceramic, as the colorants used must survive the debinding and sintering process. Moreover, it has been shown that when using pigments, i.e. predominantly crystalline inorganic substances, to colour ceramics, patchy accumulations of pigments often occur in the ceramic. As a result of this inhomogeneous distribution of the pigments, for one thing the desired colour effect is not achieved, but in addition the translucence of the ceramic is also impaired. In addition, the high local concentration of foreign material in the ceramic often results in a reduction in strength.

The processes described above are in particular not sufficiently suitable to construct, using generative processes, coloured ceramic mouldings which satisfy the demands made of dental materials. The object of the invention is therefore to provide an improved technique for the preparation of coloured ceramic mouldings in particular by means of RP processes.

SUMMARY

This object is achieved according to the invention by primary particles of oxide-ceramic material which have an average particle size in the range from 10 to 1000 nm and are treated in suspension with a chromophoric component. The term average particle size refers here to the numerical average.

DETAILED DESCRIPTION

The primary particles treated according to the invention are surprisingly suitable, when used in the preparation of ceramic mouldings, to achieve an optimally homogeneous colouring of the obtained moulding. This represents a substantial advantage compared with the ceramic materials used in the state of the art. The thus-obtained colour homogeneity is even better than the colour homogeneity obtained by using agglomerates and granular material coated with chromophoric components. Due to the high homogeneity of the colouring, an optimum colour action is achieved using only very small quantities of chromophoric component. In particular it is not necessary to operate with a surplus of chromophoric ions. The smaller quantity of chromophoric compounds required compared with the state of the art represents a further advantage of the invention in the light of the high cost of these compounds. In addition, as a result of the greater homogeneity, the number of defects in the ceramic is reduced which has a positive effect on its strength.

According to the invention, by primary particles are meant oxide-ceramic particles which have an average particle size in the range from 10 to 1000 nm ($d_{50}$=10 to 1000 nm). The average particle size is preferably in the range from 10 to 500 nm, and most preferably from 10 to 200 nm. These particles are coated with a chromophoric component.

The chemical composition of the oxide-ceramic powders used preferably includes $ZrO_2$ or $Al_2O_3$ powder or mixtures of both oxides. $ZrO_2$, $Al_2O_3$, CaO, $CeO_2$ and/or MgO-stabilized $ZrO_2$, in particular yttrium-stabilized zirconium oxide are particularly preferably used. The use of 3Y-TZP (yttrium-stabilized tetragonal zirconium dioxide polycrystals), i.e. $ZrO_2$ which is stabilized with 3 mol.-% Y203, is quite particularly preferred.

To coat the primary particles, they are firstly dispersed in a suspending agent and mixed with the chromophoric component, which must be soluble in this suspending agent.

The oxide-ceramic primary particles can be dispersed either in organic suspension media or in aqueous suspension media and further processed. As a result of the homogeneous distribution of the chromophoric components in the thus-obtained organic or aqueous suspensions, it is possible to achieve a homogeneous distribution of the chromophoric ions on the surface of the primary particles which finally results in a homogeneous colouring of the ceramic after the sintering.

In the case of organic suspensions, an organometallic compound such as e.g. an acetyl acetonate or a carboxylic acid salt which is soluble in the organic suspension medium used is preferably used as chromophoric component.

The metal ions in these organometallic compounds belong to the group of transition metals. Compounds of the elements iron, cerium, praseodymium, terbium or manganese are preferred.

Both a single organometallic compound and a combination of several compounds can be used as chromophoric component, with the result that either only one transition metal or a combination of several metals causes the specific colouring of the oxide ceramic.

Salts of carboxylic acids, acetic, propionic, butyric, 2-ethylhexylcarboxylic, stearic and palmitic acid are preferred for the organic suspensions. Above all the corresponding Fe, Pr, Mn and Tb compounds such as e.g. iron (III) acetate or acetyl acetonate, praseodymium (III) acetate or acetyl acetonate or terbium (III) acetate or acetyl acetonate and also the corresponding carboxylic acid salts are particularly preferred.

The organic-based ceramic suspension is preferably further processed by constructive RP processes such as e.g. stereolithography or 3D printing. In these processes ceramic mouldings are constructed in layers.

In aqueous suspensions, similarly to the organic suspensions, compounds of transition metals that are soluble in the aqueous suspension medium are used for colouring. But here, inorganic salts such as e.g. water-soluble nitrates and chlorides are preferably used. The same metal ions are used for colouring (Fe, Pr, Tb, Mn, Ce).

The coating of the primary particles is carried out e.g. in the manner described in EP 1 859 757 A2, which is incorporated herein in its entirety, where however there is no coating of primary particles, but a coating of prefabricated, pressable granular material.

The primary particles coated according to the invention can be produced from the finished suspension for example by carefully removing the suspending agent by evaporation. Should the coated primary particles precipitate initially in the form of aggregates or agglomerates, these can be destroyed, for example, by a customary comminution process in order to obtain the coated primary particles thus obtained. However, the finished suspension can preferably be used directly in further processing procedures as described below.

The described suspensions, which contain primary particles and the chromophoric component simultaneously, are further processed to form pressable granular material e.g. by means of spray-granulation. By already treating the primary particles with the chromophoric component before the granulation step, a homogeneous distribution of the colouring ions on the surface of the primary particles is achieved. After the granulation, which represents an agglomeration process of the primary particles, the chromophoric ions are distributed more homogeneously than previously in the individual granular particles. This represents a substantial improvement compared with the state of the art.

Aqueous ceramic suspensions are preferably used for the spray-granulation process. In addition to the chromophoric component and the suspending agent water, they preferably also contain small portions of organic components, such as temporary binders, pressing auxiliaries, dispersants and plasticizers (e.g. polyacrylates, polyvinyl alcohols, polyethylene glycol, polyvinylpyrrolidone), which serve on the one hand to optimize the granule size and on the other hand to improve the pressability of the primary particles in the further processing procedure. These organic components are preferably used in a quantity of at most 6 wt.-% (relative to the solids portion in the suspension) and do not impair the solubility of the metal salts (colour components) in water. As a result of these small organic portions, a stable suspension is obtained which, as already stated, can be further processed to form ceramic mouldings by spray-granulation but also for example in casting processes (slip-casting).

After granulation, the primary particles can be further processed to form mouldings, in particular blocks, preferably by means of dry-pressing processes. After the presintering of these oxide-ceramic spacers, they can be further processed to form dental crowns and bridge frameworks by CAD/CAM.

After coating, the particles according to the invention preferably contain 0.000001 to 0.4 wt.-%, in particular 0.0001 to 0.3 wt.-%, particularly preferably 0.01 to 0.2 wt.-%, chromophoric component, relative to the overall mass of the particles. These values always relate, irrespective of the type of transition metal compounds used (organic or inorganic), to the corresponding transition metal oxides. For example, when using iron (III) acetate or acetyl acetonate as chromophoric component, the corresponding mathematical weight percentage of $Fe_2O_3$ is given.

The chromophoric component is preferably chosen such that tooth-coloured ceramic mouldings are obtained after a sintering process. For this, in particular two or more of the above-named transition metal compounds can be combined to achieve a specific shade.

The organic suspensions are preferably used for the preparation of oxide-ceramic mouldings by means of rapid prototyping processes, such as e.g. stereolithography, 3D printing or selective laser sintering. The advantage of these constructive processes compared with cutting techniques is that less valuable oxide-ceramic material is used. In RP processes, only as much material as is required for the specific ceramic spacer is used. In contrast, in cutting techniques the material consumption is higher because the specific geometry of the dental component is machined from a ceramic base body (block, plate, cylinder) and thus there is a much higher material consumption.

The ceramic mouldings prepared by means of RP processes are composed of a stable organic matrix in which the oxide-ceramic primary particles are distributed and embedded homogeneously. The organic matrix must have a minimum strength such that the required dimensional stability of the components is ensured during further processing.

The aqueous suspensions are processed, preferably by means of spray-drying, to prepare granular material. In this process, the suspending agent water evaporates, thus effecting a coating of the primary particles with the colouring components. The agglomeration of the primary particles takes place at the same time in the spray-granulation process, with the result that the spray-drying leads to granular material which consists of primary particles that are coated with chromophoric ions. This granular material can then be dry-pressed to form ceramic blocks and further processed using CAD/CAM.

If aqueous suspensions are used in the slip-casting process for the preparation of ceramic cast parts, the suspension is poured into a mould, the casting is then dried and sintered. The water evaporates in the drying process and the primary particles coated with the chromophoric component form a porous moulding.

Only during the sintering are the transition metal ions incorporated into the crystal lattice, e.g. of the $ZrO_2$ ceramic, from which the colouring of the ceramic results. This applies to all processes irrespective of the type of suspension (organic or aqueous) and irrespective of the type of technical process used (RP process, spray-granulation, casting process).

In order to achieve a homogeneous distribution of the particles in the support medium and to destroy particle aggregates and agglomerates, the oxide-ceramic powder is preferably subjected to a homogenization and comminution process before treatment with the chromophoric component. This can be a grinding process in a mill customary for ceramic powders or a dispersion process using ultrasound. In this process, e.g. mills, in particular attritors, dissolvers or ultrasound dispersers are used.

The homogenization or comminution process is preferably carried out in the presence of the desired suspension medium. During this process, the chromophoric and optionally stabilizing components are added to the suspension and the mixture comminuted and homogenized in the course of the process. The finished suspension is then used as described above in further processing procedures (RP process, spray-granulation).

The invention also relates to the use of the primary particles treated according to the invention. The primary particles are generally suitable for use in the most varied processes for the preparation of ceramic mouldings and in particular dental restorations such as e.g. inlays, onlays, veneers, crowns, bridges or frameworks, for example by dry-pressing and subsequent sintering. In these processes, the treated primary particles are preferably used in the form of granular material which contains the primary particles according to the invention. Suitable granular material can be obtained in particular by the spray-drying described above.

Examples of further preferred processes are rapid prototyping (RP) processes, such as stereolithography, 3D printing or selective laser sintering. These processes are particularly advantageous because, as non-cutting techniques, they avoid the loss of material associated with cutting techniques. For use in these techniques, the primary particles according to the invention are typically used in the form of a liquid suspension, in particular a liquid organic slip or a ceramic ink.

A suspension based on oxide-ceramic material which contains 10-95 wt.-%, preferably 40-90 wt.-%, particularly preferably 70-85 wt.-% primary particles according to the invention and 5-90 wt.-%, preferably 7-80 wt.-%, most preferably 10-20 wt.-% organic component, each relative to the overall mass of the suspension, is preferred.

A suspension which contains
(A) 10-95 wt.-%, preferably 40-90 wt.-%, particularly preferably 70-85 wt.-% primary particles according to the invention,
(B) 3-85 wt.-%, preferably 5-40 wt.-%, particularly preferably 7-15 wt.-% polyreactive binder,
(C) 1 to 80 wt.-%, preferably 1.5 to 20 wt.-%, particularly preferably 2 to 10 wt.-% organic solvent and
(D) 1 to 30 wt.-% further auxiliaries and additives,
in each case relative to the overall mass of the suspension is particularly preferred.

A mixture of primary particles according to the invention with different chromophoric components can optionally be used as primary particles (A).

In particular polymerization and polyaddition resins which as a rule are composed of a mixture of low-molecular or oligomeric monomers which contain one or more polyreactive groups can be used as polyreactive binder (B).

In the case of polymerization resins, radically and cationically polymerizable resins and monomers are preferably used for ring-opening metathesis polymerization. In the case of the polyaddition resins, Michael reaction resins are above all suitable.

In particular mono- or multifunctional (meth)acrylates, mono- and bis(meth)acrylamides or their mixtures can in particular be used as radical polymerization resins. Di- or multifunctional acrylates are preferably used in the organic suspension in mixture with monoacrylates.

Components which have a boiling point of at least approx. 120° C, preferably from 150 to 250° C., particularly preferably from 180 to 230° C., are preferably used as organic solvent (C) with the result that a stereolithographic processing of the suspension does not result in an early evaporation. Mixtures of solvents which can be progressively evaporated in a temperature range between 150 and 250° C. are particularly suitable. Quite particularly suitable are octanol, triethylene glycol divinylether, 2-amino-2-methyl-1-propanol, 2-methyl-2,4-pentanediol, ammonium citrate tribasic (solid), tripropylene glycol, tetraethylene glycol, triethylene glycol, triethyl citrate, ethyl acetoacetate, cyclohexanol, cyclohexanone, diethylene glycol monomethyl ether, dibutyl oxalate, 2,5-dimethoxytetrahydrofuran, polyethylene glycol 300, 1- or 2-nonanol, diethylene glycol diethylether, 2,5-dimethoxytetrahydrofuran, dibutyl oxalate, cyclohexanol, cyclohexanone, ethyl acetoacetate and mixtures thereof.

It was found that the evaporation of the above solvents leads to the formation of micropores in the green body which then close again upon sintering but which also make possible and promote the escape of gases in the debinding step and thus prevent the formation of stresses and cracks. Moreover, the danger of a separation of the stereolithographically produced layers is reduced and a complete removal of the organic components favoured.

Alternatively, a porosity of the green body can also be achieved by removing by extraction elutable portions before heat treatment. Suitable extractable components are water-soluble polymers such as e.g. polyvinyl alcohol, polyvinyl pyrrolidone and polyethylene glycols. Furthermore, benzine-soluble substances such as paraffins or waxes and long-chained fatty acid esters can be used. The preferred quantity of extractable components in the resin matrix is between 0 and 40 wt.-%, particularly preferably between 0. 1 and 30 wt.-%, relative to component (B).

In addition to components (A) to (C), the suspensions according to the invention can contain further components (D) as additives.

The suspension according to the invention usually contains an initiator, in particular a photoinitiator. The choice of photoinitiator depends on the type of monomer used. Suspensions based on radically-polymerizable resins can be polymerized with the known radical photoinitiators for the visible range (cf. J. P. Fouassier, J. F. Rabek (eds.), Radiation Curing in Polymer Science and Technology, Vol. II, Elsevier Applied Science, London and New York (1993), which is hereby incorporated by reference in its entirety), such as e.g. acyl or bisacylphosphine oxides, preferably with α-diketones such as 9,10-phenanthraquinone, diacetyl, furil, anisil, 4,4'-dichlorobenzil and 4,4'-dialkoxybenzil, and particularly preferably camphorquinone. To accelerate the initiation α-diketones are preferably used in combination with aromatic amines. Redox systems which have proved particularly worthwhile are combinations of camphorquinone with amines such as N,N-dimethyl-p-toluidine, N,N-dihydroxyethyl-p-toluidine, 4-dimethylaminobenzoate or structurally related systems. The initiators are preferably used in a quantity of 0.00 1-1.0 wt.-%, in particular 0.01 to 1.0 wt.-%, particularly preferably 0.1 to 1.0 wt.-%, in each case relative to the overall mass of the suspension.

Furthermore the suspension can also contain an inhibitor as stabilizer to prevent a spontaneous polyreaction. The inhibitors or stabilizers improve the storage stability of the suspension and in the case of stereolithography also prevent an uncontrolled polyreaction in the stereolithographic tank. The inhibitors are preferably added in such a quantity that the suspensions are storage-stable over a period of approx. 2-3 years. The inhibitors are particularly preferably used in a quantity of 0.001 to 1.0 wt.-%, quite particularly preferably 0.001 to 0.50 wt.-%, in each case relative to the overall mass of the suspension.

According to a further preferred embodiment, the suspensions contain a so-called debinding accelerator. The latter is preferably used in a quantity of 0 to 20 wt.-%, particularly preferably 0.01 to 10 wt.-%, in each case relative to the overall mass of the suspension. By debinding accelerators are meant substances which facilitate the removal of the binder during the debinding process.

According to the invention, comonomers which lead to a reduction in the thermal stability of polymer networks can also advantageously be used as debinding accelerators. Comonomers which contain thermally labile groups, such as e.g. peroxide, azo or urethane groups, which are incorporated into the polymer network during the stereolithographic process and then accelerate the degradation of the polymer network in the thermal debinding process are suitable for this. A preferred example of a polymerizable peroxide is 4,4'-divinyl benzoyl peroxide. A preferred example of a polymerizable azo compound is the ester of 2-hydroxyethyl methacrylate and 4,4'-azobis-(4-cyanovaleric acid). Moreover, comonomers the polyreaction products of which are readily thermally degradable are suitable as debinding accelerators. Comonomers which like α-methylstyrene have a low ceiling temperature $T_c$ are preferred for radical polymerization resins. The ceiling temperature is the limit temperature at which the polymerization is in equilibrium with the depolymerization and can be calculated from the quotient of the polymerization enthalpy and the polymerization entropy (cf. H.-G. Elias, Makromoleküle, Vol. 1, 6$^{th}$ ed., Wiley-VCH, Weinheim etc. (1999), 193 et. seq., which is hereby incorporated by reference in its entirety).

The suspension according to the invention can also contain one or more dispersants which prevent the formation of agglomerates and the settling of the ceramic particles. Preferred dispersants are above all polymers, in particular polyelectrolytes, e.g. polycarboxylic acids or polycarboxylic acid salts, or non-ionic polymers, such as e.g. polyethylene glycol or carboxymethylcellulose. Polyelectrolytes which, like e.g. ammonium polycarboxylate, carry ionic groups and which therefore adsorb relatively easily on the surface of solids, e.g. on ceramic particles, are suitable as dispersants. The polyelectrolyte ions can then give the particles an electric charge, which is then referred to as an electrosteric effect. The preferred quantity of dispersant is 0.1 to 5 wt.-%, in each case relative to the mass of component (A).

The suspensions according to the invention can contain one or more plasticizers as further components. The plasticizer(s) can optionally prevent the ceramic green body from becoming brittle after the photochemical curing and a possible drying. Plasticizers also ensure a sufficient flexibility of the stereolithographically produced green body. Preferred plasticizers are phthalates, such as e.g. dibutyl- or dihexyl phthalate, non-acid phosphates, such as e.g. tributyl or tricresyl phosphate, n-octanol, glycerol or polyethylene glycols. Plasticizers are preferably used in a quantity of 0 to 15 wt.-% and particularly preferably 0. 1 to 5 wt.-%, relative to the mass of component (B).

Furthermore, the suspensions according to the invention can contain components which promote the oxidative degradation of the polymer matrix during the debinding process, such as e.g. in the case of peroxides stable at room temperature, or also catalytic components which make possible a catalytic debinding. In addition to peroxides, other substances which have an oxidizing effect, such as e.g. nitric acid, or which split or form oxidants, are also suitable.

The rheological properties of the suspension according to the invention are preferably set such that their viscosity lies in the range of from 200 mPa·s to 2,000 Pa·s, preferably 500 mPa·s to 500 Pa·s, more preferably 500 mPa·s to 50 Pa·s, most preferably 200 to 20000 mPa·s, and particularly preferably 500 to 5000 mPa·s. It is advantageous if there are no yield points if at all possible. The viscosity is determined at 23° C. with a plate-plate viscometer.

The invention also relates to the use of a suspension according to the invention for the preparation of ceramic mouldings and in particular dental restorations, such as e.g. inlays, onlays, veneers, crowns, bridges or frameworks.

The invention also relates to a process for the preparation of a ceramic moulding in which
(a) a green body is prepared by curing a suspension according to the invention by local introduction of radiation energy with formation of the geometric shape of the green body,
(b) the green body is subjected to a heat treatment to remove the binder (debinding), in order to obtain a white body, and
(c) the white body is sintered.

The preparation of the green body in step (a) takes place by rapid prototyping, preferably by stereolithography. A ceramic green body is prepared by layered radiation curing of a suspension according to the invention, in particular of a free-flowing ceramic slip, which is debound in step (b). The binder used is removed by heating the green body to a temperature of preferably 90° C. to 600° C., and the so-called white body is obtained. The white body is sintered in step (c) to form a dense ceramic moulding. The sintering of the white body takes place in the sintering furnace, preferably at a temperature of 1100 to 1600° C., preferably 1400 to 1500° C., for zirconium dioxide, from 1400 to 1800° C., preferably 1600 to 1700° C. for aluminium oxide and from 650 to 1100° C., preferably 700 to 900° C. for glass ceramic. The ceramic mouldings prepared according to the process according to the invention are characterized by a high strength and great detail accuracy. The bending strength according to ISO 6872 is more than 500 MPa, in particular in the range from 800 to 1100 MPa, for mouldings made of $ZrO_2$. Mouldings made of $Al_2O_3$ have a bending strength of preferably more than 300 MPa, in particular in the range from 500 to 700 MPa and mouldings made of glass ceramic preferably over 100 MPa, in particular in the range from 150 to 500 MPa.

The invention is explained in more detail below by means of examples.

EXAMPLE 1

Basic Composition of 3Y-TZP Ceramic Slips

| Component | Ex. 1A [wt.-%] | Ex. 1B [wt.-%] | Ex. 1C [wt.-%] | Ex. 1D [wt.-%] |
|---|---|---|---|---|
| 3Y-TZP[1] | 83.0 | 83.0 | 83.0 | 83.0 |
| Manganese (III) acetylacetonate[1] | 0.1 | | | |
| Iron (III) acetylacetonate[1] | | 0.1 | | |
| Terbium (III) acetylacetonate[1] | | | 0.1 | |
| Praseodymium (III) acetylacetonate[1] | | | | 0.1 |
| Triphenylol propane triacrylate | 3.5 | 3.5 | 3.5 | 3.5 |
| Phenoxy-diethylene glycol diacrylate | 3.0 | 3.0 | 3.0 | 3.0 |
| Polyethylene glycol diacrylate | 3.99 | 3.99 | 3.99 | 3.99 |
| Octanol | 3.0 | 3.0 | 3.0 | 3.5 |
| Disperbyk | 1.0 | 1.0 | 1.0 | 1.0 |
| Tert-butylperoxy-2-ethyl-hexanonate | 0.1 | 0.1 | 0.1 | 0.1 |

[1]In the form of primary particles coated with the respective transition metal salt Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. Primary particles of oxide-ceramic material, wherein the primary particles have an average particle size in the range from 10 to 1000 nm and are coated with a chromophoric component which comprises an acetyl acetonate of the elements iron, cerium, praseodymium, terbium, lanthanum, tungsten, osmium or manganese, wherein the particles contain 0.000001 to 0.4 wt.-% chromophoric component, relative to the overall mass of the primary particles, wherein the primary particles are binder-free.

2. The primary particles according to claim 1, wherein the oxide-ceramic material comprises $ZrO_2$.

3. The primary particles according to claim 1, wherein the oxide-ceramic material comprises $ZrO_2$ stabilized with $Y_2O_3$.

4. The primary particles according to claim 1, wherein the chromophoric component comprises iron (III) acetylacetonate, or manganese (III) acetylacetonate, or praseodymium (III) acetylacetonate or terbium (III) acetylacetonate.

5. The primary particles according to claim 1, which have an average primary particle size in the range 10 to 500 nm.

6. The primary particles according to claim 5, wherein the average primary particle size is in the range from 10 to 200 nm.

7. Granular material comprising an oxide-ceramic material, which comprises primary particles according to claim 1.

* * * * *